United States Patent [19]

Araps

[11] 4,171,311
[45] Oct. 16, 1979

[54] IMIDES OF THYROXIN AND TRIIODOTHYRONINE

[75] Inventor: Constance J. Araps, San Jose, Calif.

[73] Assignee: International Diagnostics Tech. Inc., Santa Clara, Calif.

[21] Appl. No.: 869,824

[22] Filed: Jan. 16, 1978

[51] Int. Cl.² .......................................... C07D 405/12
[52] U.S. Cl. ........................ 260/326.34; 260/326 C; 260/326 D; 260/112.5 TR; 260/112 T
[58] Field of Search .......... 260/326 D, 326 C, 326.34; 546/99

[56] References Cited

U.S. PATENT DOCUMENTS 3,679,653  7/1972  Schudl ................................ 424/178

OTHER PUBLICATIONS

Gussakovskii et al., Chem. Abs., 80, 60173v, (1973).

Primary Examiner—Mark L. Berch
Attorney, Agent, or Firm—Limbach, Limbach & Sutton

[57] ABSTRACT

New fluorescently labeled thyroxin and triiodothyronine for use in competitive binding fluorescent assays of blood sera for thyroxin and triiodothyronine are described. The new materials have the structural formula:

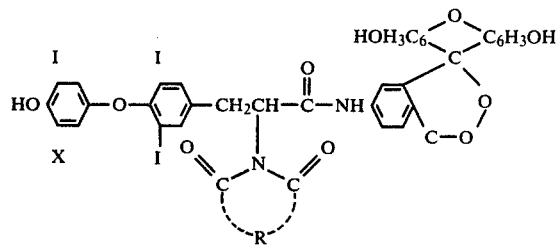

in which X is H or I and R represents the atoms completing a cyclic anhydride structure.

2 Claims, No Drawings

IMIDES OF THYROXIN AND TRIIODOTHYRONINE

BACKGROUND OF THE INVENTION

Thyroxin and triiodothyronine are hormones secreted by the thyroid gland. They enter the bloodstream where they are reversibly bound by plasma proteins. Numerous diseases, most of which involve the thyroid gland, cause abnormal levels of these hormones in the blood plasma. Determination of the quantity of these hormones in the blood plasma provides information useful in the diagnosis and treatment of diseases which affect the levels of these materials in the blood plasma.

The thyroid hormones in blood serum have been measured by competitive protein binding. For example, thyroxin extracted from a measured quantity of blood serum and a measured quantity of thyroxin labeled with either a radioactive element or with a fluorescent material are permitted to react with and come to equilibrium with a measured quantity of antibody to thyroxin. Thyroxin bound to the antibody is separated from thyroxin not bound to the antibody and the amount of labeled thyroxin in either the bound or unbound thyroxin portions is determined from the amount of labeled thyroxin found in either the bound or unbound portions of the product. The quantity of thyroxin in the serum can then be determined.

Heretofore, most thyroid hormone analyses have been made using thyroxin labeled with radioactive iodine by the competitive protein binding method. Fluorescent assays are superior to radio assay in several respects, e.g., personal safety, low capital investment and stability of materials. The adoption of fluorescent assay methods has been impeded by unavailability of suitable fluorescent labeled thyroxin, adequate separation of bound from unbound thyroxin and insufficiently sensitive fluorometers.

U.S. Pat. No. 3,992,631 describes a sensitive fluorometer useful in fluorescent assays. Highly suitable fluorescently labeled hormones have now been developed and have been found to work satisfactorily in a competitive protein binding analysis.

BRIEF DESCRIPTION OF THE INVENTION

Fluorescently labeled thyroxin and triiodothyronine suitable for use in a competitive protein binding analysis have been prepared by reacting thyroxin or triiodothyonine with an anhydride of a cyclic polycarboxylic acid to form derivatives of the hormone and the derivatives are then reacted with fluorescein amine to form the fluorescently labeled hormone which has the structure shown in the abstract above.

DETAILED DESCRIPTION OF THE INVENTION

The derivatives of the hormones were prepared according to the following reaction:

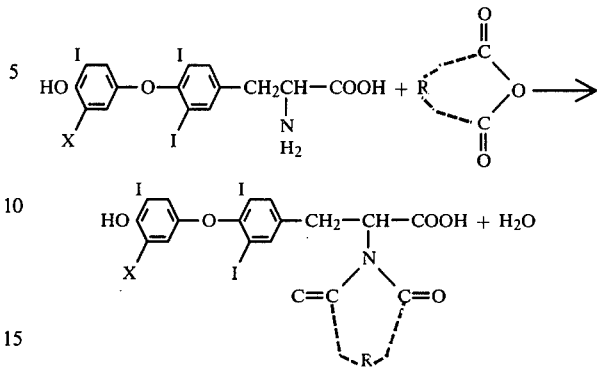

X is H or I and R represents the atoms completing a cyclic anhydride structure.

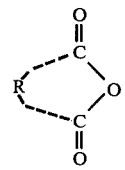

may be the anhydride of O-phthalic acid, naphthalic acid, cyclohexane dicarboxylic acid, succinic acid, maleic acid, malic acid and the like which are derived from vicinal cyclic dicarboxylic acids.

Preparation of Phthaloyl Derivatives 0.64 mols of thyroxin and 0.64 mols of finely ground phthalic anhydride were suspended in dry toluene and 0.015 ml. of a saturated solution of triethylamine in toluene were added. The mixture was refluxed for four hours over a Dean Stark trap which removed water as an azeotrope. The mixture was cooled, concentrated to dryness on a rotary evaporator and the resulting solids triturated with a solution of 100 ml. of water containing 1 ml. of concentrated hydrochloric acid. The solid product mixture was isolated by filtration and air dried and constituted a mixture of unreacted thyroxin and the desired product. The solid was boiled in 95% ethanol to selectively dissolve the phthalimide derivative, and the hot mixture was centrifuged immediately. The hot filtrate was diluted with distilled water until a precipitate was deposited and then cooled for 16 hours. Ultraviolet and infrared inspection of the product were consistent with the structure indicated for the phthaloyl derivative in the equation above.

Coupling of the Phthaloyl Derivative of Tyroxin with Fluorescein Amine

The phthaloyl derivative of thyroxin prepared above was coupled to fluorescein amine according to the following equation:

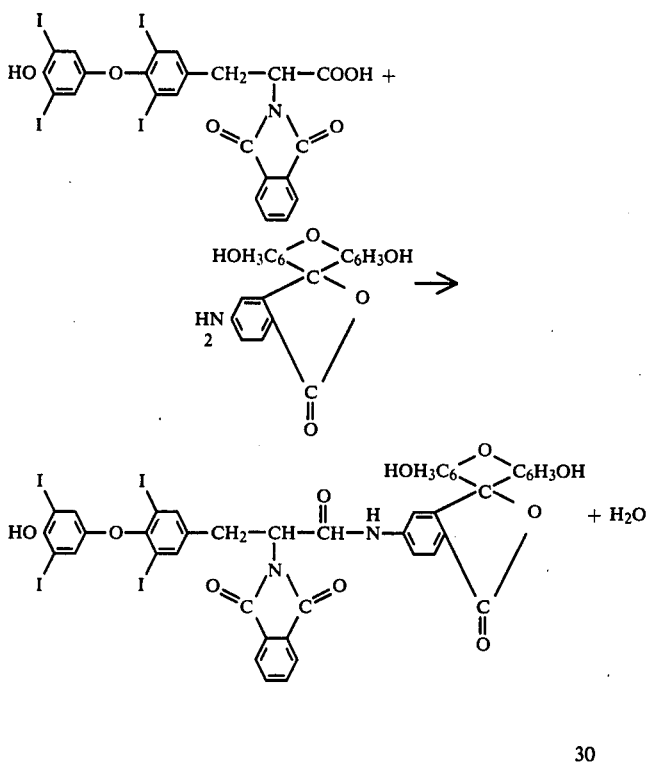

38 mg. of the phthaloyl derivative, 29.2 mg. of fluorescein amine and 8.7 mg. of dicyclohexylcarbodiimide were added to a solvent which was a 50/50 mixture of dichloromethane and acetonitrile. The reaction mixture was shaken for 48 hours and then centrifuged. The filtrate was collected and the solids were washed three times with 2 ml. portions of acetonitrile. The combined washings and the filtrate were concentrated to an orange paste by evaporation and redissolved in 95% ethanol for ultraviolet spectral analysis. Ultra violet spectrum examination indicated the product to conform to the structure of the product shown in the above equation.

The fluorescently labeled product was mixed with varying amounts of standard antibody (for thyroxin) solution found to conjugate with it.

Mixtures of the fluorescently labeled product and non-fluorescent thyroxin were mixed with varying amounts of standard antibody and competitive reaction of non-fluorescent thyroxin and the fluorescently labeled thyroxin with the antibody was demonstrated.

Other cyclic anhydrides such as naphthalic anhydrides, cyclohexane dicarboxylic anhydride, succinic anhydride, maleic anhydride and malic anhydride react with thyroxin and triodothyronine under dehydrating conditions in the same manner as does phthalic anhydride to form water and a product containing the imide of the hormone and the anhydride.

An intermediate in the reaction sequence is an amic acid of the structure

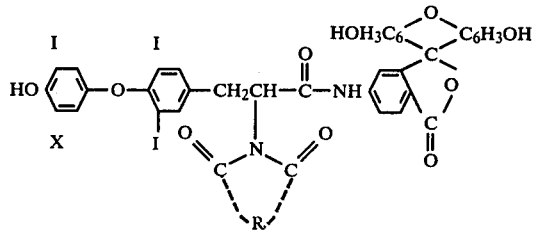

Dehydrating conditions cyclize the amic acid to imide via irreversible removal of water.

In the above example, the reaction temperature was that of refluxing toluene and the time was four hours. Water was removed as a toluene azeotrope by means of a Dean Stark trap. This product can be reacted with fluorescein amine to provide a fluorescently labeled hormone suitable for use in competitive protein binding analysis. The imide need not be further purified.

I claim:

1. Compounds having the formula in which X is H or I and R represent the atoms completing an imide of a cyclic dicarboxylic acid selected from the group consisting of o-phthalic acid, naphthalic acid, cyclohexane dicarboxylic acid, succinic acid, maleic acid, and malic acid.

2. Fluorescently labeled thyroxin or triiodothyronine prepared by heating thyroxin or triiodothyronine with the anhydride of a vicinal cyclic dicarboxylic acid selected from the group consisting of o-phthalic acid, naphthalic acid, cyclohexane dicarboxylic acid, succinic acid, maleic acid amd malic acid to cause reaction between the anhydride and the $NH_2$ group of the thyroxin or triiodothyronine and then reacting the resultant imide with fluorescein amine.

* * * * *